United States Patent [19]

Volkamer et al.

[11] 4,320,232
[45] Mar. 16, 1982

[54] PROCESS FOR CONJOINTLY PREPARING METHYL TERT.-BUTYL ETHER AND OBTAINING ISOBUTENE

[75] Inventors: Klaus Volkamer, Frankenthal; Alfred Lindner, Bobenheim-Roxheim; Franz Merger, Frankenthal; Ulrich Wagner, Limburgerhof; Erwin Brunner, Ludwigshafen; Gerhard Sandrock, Frankenthal; Max Strohmeyer, Limburgerhof, all of Fed. Rep. of Germany

[73] Assignee: BASF Aktiengesellschaft, Fed. Rep. of Germany

[21] Appl. No.: 161,041

[22] Filed: Jun. 19, 1980

[30] Foreign Application Priority Data

Jul. 14, 1979 [DE] Fed. Rep. of Germany ....... 2928509

[51] Int. Cl.$^3$ ............................................. C07C 41/06
[52] U.S. Cl. .................................. 568/697; 568/907; 585/639
[58] Field of Search ........................................ 568/697

[56] References Cited

U.S. PATENT DOCUMENTS

| | | |
|---|---|---|
| 3,119,766 | 1/1964 | Voltz et al. ........................ 568/697 |
| 3,121,124 | 2/1964 | Verdol . |
| 3,170,000 | 2/1965 | Verdol . |
| 3,629,478 | 12/1971 | Haunschild ........................ 568/697 |
| 3,637,889 | 1/1972 | Watanabe et al. . |
| 3,979,461 | 9/1976 | Ancillotti et al. ................... 568/697 |
| 4,071,567 | 1/1978 | Ancillotti et al. ................... 568/697 |
| 4,242,526 | 12/1980 | Laky et al. ......................... 568/697 |

FOREIGN PATENT DOCUMENTS

| | | |
|---|---|---|
| 26625 | 6/1977 | Australia . |
| 1165479 | 10/1969 | United Kingdom . |
| 1173128 | 12/1969 | United Kingdom . |
| 1176620 | 1/1970 | United Kingdom . |

Primary Examiner—Joseph E. Evans
Attorney, Agent, or Firm—Keil & Witherspoon

[57] ABSTRACT

A process for conjointly preparing methyl tert.-butyl ether and obtaining isobutene from an isobutene-containing $C_4$-hydrocarbon mixture. In the process the $C_4$-hydrocarbon mixture is reacted, in one or more etherification stages, with methanol and a primary $C_3$- or $C_4$-alcohol in the presence of an acid condensing agent, the resulting reaction mixture or mixtures are then separated into a fraction containing the unconverted hydrocarbons, the methyl tert.-butyl ether and a fraction containing the $C_3$- or $C_4$-alkyl tert.-butyl ether. Thereafter, the $C_3$- or $C_4$-alkyl tert.-butyl ether is decomposed at an elevated temperature, in the presence of an acid catalyst, into isobutene and primary $C_3$- or $C_4$-alcohol.

12 Claims, 1 Drawing Figure

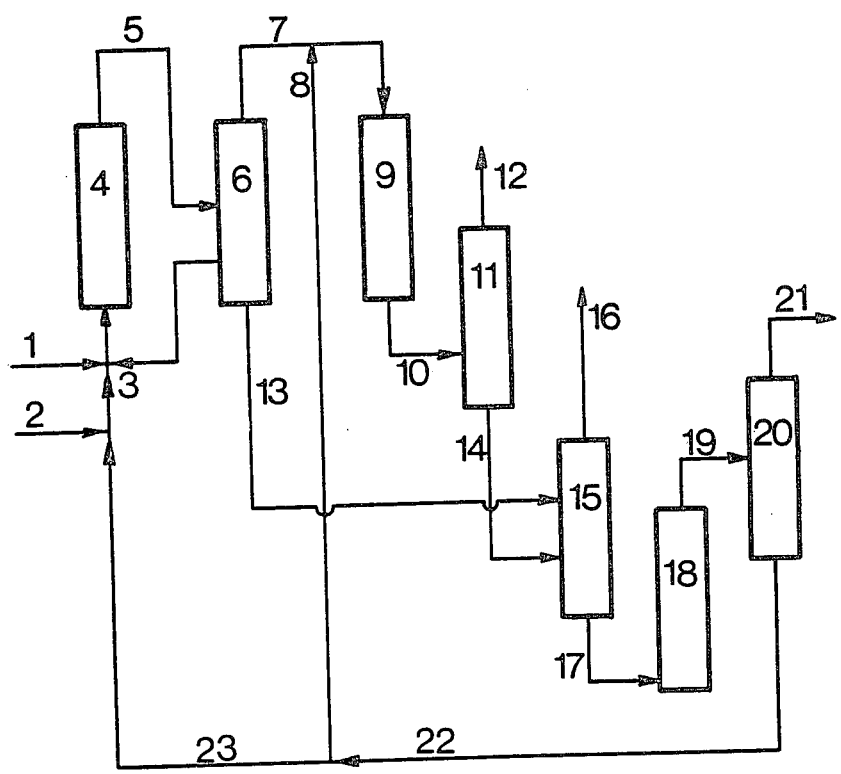

PROCESS FOR CONJOINTLY PREPARING METHYL TERT.-BUTYL ETHER AND OBTAINING ISOBUTENE

The present invention relates to a process for conjointly preparing methyl tert.-butyl ether and obtaining isobutene from an isobutene-containing $C_4$-hydrocarbon mixture.

The preparation of methyl tert.-butyl ether by reacting an isobutene-containing $C_4$-hydrocarbon mixture with methanol has been disclosed, for example in German Laid-Open Application DOS 2,629,769. In preparing methyl tert.-butyl ether, which is increasingly being used as a fuel additive for improving the octane number, it is a disadvantage that on removing the unconverted hydrocarbons from the reaction mixture by distillation, the hydrocarbons obtained contain about 2% of methanol (due to hydrocarbon/methanol azeotropes), which can only be recovered by expensive methods, for example by interpolating a water wash into the sequence.

A process for obtaining isobutene has also been disclosed, for example in German Pat. No. 1,216,865 and German Published Applications DAS 1,934,422 and DAS 2,011,826, in which, in a first stage, an isobutene-containing $C_4$-hydrocarbon mixture is reacted with methanol and, in a second stage, the methyl tert.-butyl ether formed is decomposed into methanol and isobutene. However, the known processes for obtaining isobutene have the disadvantage that in addition to the formation of azeotropic mixtures of methanol and the unconverted hydrocarbons in the ether-forming stage, as already described above, an azeotropic mixture of methanol and isobutene is also formed during distillative separation of the reaction mixture, consisting of isobutene and methanol, obtained from the decomposition stage, so that in the decomposition stage the isolation of the methanol is again very difficult and requires, for example, interpolating an expensive water wash. The known processes for obtaining isobutene by decomposing the tertiary ether obtained in a first (etherification) stage have not been put to industrial use, because of the above disadvantages.

On an industrial scale, isobutene has hitherto been obtained from $C_4$-hydrocarbon mixtures only by using sulfuric acid extraction processes. In these processes, however, sulfuric acid of a high concentration must be used, and expensive materials therefore have to be employed for the equipment. Since, furthermore, side-reactions of isobutene, for example dimerization, polymerization, hydration and the like, occur during extraction, the sulfuric acid extraction process is not always satisfactory in respect of the yield and quality of the products.

It is an object of the present invention to provide a process for conjointly preparing methyl tert.-butyl ether and obtaining isobutene from isobutene-containing $C_4$-hydrocarbon mixtures.

According to the invention, this and other objects and advantages are achieved in a process for preparing methyl tert.-butyl ether and obtaining isobutene from isobutene-containing $C_4$-hydrocarbon mixtures, wherein (a) the $C_4$-hydrocarbon mixture is reacted, in one or more etherification stages, with methanol and a primary $C_3$- or $C_4$-alcohol in the presence of an acid condensing agent, (b) the resulting reaction mixture or the resulting reaction mixtures are then separated into
a fraction containing the unconverted hydrocarbons, the methyl tert.-butyl ether and
a fraction containing the $C_3$- or $C_4$-alkyl tert.-butyl ether and (c) thereafter the $C_3$- or $C_4$-alkyl tert.-butyl ether is decomposed at an elevated temperature, in the presence of an acid catalyst, into isobutene and primary $C_3$- or $C_4$-alcohol.

Using the novel process, a $C_4$-hydrocarbon raffinate which is virtually free from $C_3$- or $C_4$-alcohol can be isolated, from the reaction mixture obtained after the etherification stage, by simple distillation without interpolating a water wash, since unconverted primary $C_3$- or $C_4$-alcohol surprisingly does not form an azeotrope with the $C_4$-hydrocarbons. In general, the concentration of $C_3$- or $C_4$-alcohol in the $C_4$-hydrocarbon raffinate is not more than 1,000 ppm by weight, preferably not more than 200 ppm by weight, in particular not more than 20 ppm by weight. It is also surprising that the $C_4$-hydrocarbon raffinate obtained in the process according to the invention by distillation without interpolating a water wash has a lower methanol concentration than is obtained on etherification with methanol alone, because of the formation of hydrocarbon/methanol azeotropes, described above. In general, the process according to the invention gives a $C_4$-hydrocarbon raffinate having a methanol content of less than 1% by weight, preferably less than 0.5% by weight. Surprisingly, on distillative separation of the reaction mixture, obtained on decomposing the $C_3$- or $C_4$-alkyl tert.-butyl ether, into isobutene and $C_3$ or $C_4$-alcohol, no azeotropes of the alcohol with isobutene are formed either. The isobutene can therefore be obtained in a very pure form. In general, the isobutene is taken off as the top product of the distillation and contains not more than 100 ppm by weight, preferably not more than 50 ppm by weight, in particular not more than 20 ppm by weight, of $C_3$- or $C_4$-alcohol. The $C_3$- or $C_4$-alcohol can therefore be recovered simply, and virtually without losses, without interpolating a water wash, and be recycled to the etherification stage.

A further advantage of the present process is the great flexibility of the plant for utilizing the isobutene contained in the $C_4$-hydrocarbon starting mixture, as the plant can easily be adapted to suit fluctuating market demand for isobutene and methyl tert.-butyl ether.

Using the process of the invention, the isobutene is obtained in high yield, based on primary $C_3$- or $C_4$-alcohol employed. It was surprising that this high yield should be achievable with a higher alcohol, such as a primary $C_3$- or $C_4$-alcohol, since it known from U.S. Pat. No. 3,170,000, especially Table I, that on reaction of $C_5$-hydrocarbon mixtures with alcohols, substantially poorer yields of tertiary ether are obtained when using $C_3$- or $C_4$-alcohols than when using ethanol or methanol.

Suitable isobutene-containing $C_4$-hydrocarbon mixtures for the process according to the invention are obtained, for example, from the thermal or catalytic cracking of petroleum products, from the preparation of ethylene by pyrolysis of liquefied petroleum gas (LPG), light gasoline (naphtha), gas oil or the like, or from the catalytic dehydrogenation of n-butane and/or n-butene. These $C_4$-hydrocarbon mixtures as a rule contain olefinic and paraffinic $C_4$-hydrocarbons in addition to the isobutene and can furthermore contain butadiene, for example in an amount of up to 70% by weight, and higher acetylenes, eg. but-1-yne and butenyne. Butadiene-containing $C_4$-hydrocarbon mixtures can be used as such or after first removing the butadiene from the mixture, for example by extraction using a selective solvent. The $C_4$-hydrocarbon mixtures may in addition contain $C_3$-hydrocarbons, eg. propane, propene and propyne, for example in amounts of up to 10% by weight. In general, the $C_4$-hydrocarbon mixtures contain from 5 to 95% by weight, preferably from 10 to 90% by weight, especially from 20 to 70% by weight, of isobutene. Preferred $C_4$-hydrocarbon mixtures contain isobutene together with n-butane, isobutane, but-1-ene, trans-but-2-ene and cis-but-2-ene, with or without buta-1,3-diene.

The primary $C_3$- or $C_4$-alcohols (ie. alcohols of 3 or 4 carbon atoms) used according to the invention are in general n-propanol, n-butanol or isobutanol, preferably n-propanol or isobutanol, more especially the latter. The $C_3$- or $C_4$-alcohols and the methanol employed according to the invention are used, for example, as technical-grade products of the usual purity, for example a purity of not less than 95%, preferably not less than 98%.

Examples of suitable acid condensing agents for the etherification which constitutes the first stage are mineral acids, eg. sulfuric acid and phosphoric acid, organic sulfonic acids, eg. benzenesulfonic acid and p-toluenesulfonic acid, acid aluminum salts and acid catalysts of the Friedel-Crafts type, eg. copper(II) chloride and iron(III) chloride, and also, preferably, ion exchangers in the hydrogen form. Examples of suitable ion exchangers are sulfonated coal, sulfonated phenol-formaldehyde resins, sulfonated resins derived from coumarone-indene condensates and, in particular, sulfonated polystyrene resins, eg. nuclear-sulfonated cross-linked styrene-divinylbenzene copolymers. If a liquid or dissolved acid condensing agent is used, the amount thereof is in general from about 0.001 to 0.9 liter, preferably from 0.01 to 0.7 liter, per liter of reactor volume. If solid acid condensing agents are used, the amount thereof is in general from 0.01 to 1 liter (bulk volume) per liter of reactor volume. The solid acid condensing agents may be used unsupported or on a carrier. Examples of suitable carriers are aluminum oxide, silica, active charcoal and organic polymers. The etherification may be carried out in, for example, stirred kettle reactors or fixed bed reactors, the latter being preferred.

To effect the etherification, the $C_4$-hydrocarbon mixture is reacted with the primary $C_3$- or $C_4$-alcohol and methanol in the presence of the acid condensing agent, in general at from 20° to 120° C., preferably from 20° to 100° C., especially from 30° to 80° C. It is particularly advantageous to choose the temperature pattern in the etherification stage in such a way that the exit temperature of the reaction mixture from this stage is from 20° to 100° C., preferably from 20° to 65° C., especially from 30° to 50° C. Preferably, the exit temperature is lower than the reaction temperature in the middle zone and/or starting zone of the etherification.

The etherification according to the invention may be carried out under atmospheric pressure but it is advantageous to work under slightly superatmospheric pressure, for example at from 1.01 to 30 bar, especially from 2 to 20 bar. The isobutene-containing $C_4$-hydrocarbon mixture may, depending on the pressure and temperature, be employed for the reaction as a liquid or a gas. Preferably, liquid isobutene-containing $C_4$-hydrocarbon mixtures are employed. The etherification can be carried out batchwise. In this case, the reaction time is in general from 1 minute to 5 hours. Preferably, however, the etherification is carried out continuously, the ratio of the reactor volume in liters to the throughput in 1/h being, in general, from 0.01 to 5 hours, preferably from 0.05 to 1 hour.

For the etherification, the methanol and the $C_3$- or $C_4$-alcohol are in general employed in a weight ratio of from 1:50 to 50:1, preferably from 1:20 to 20:1, especially from 1:10 to 10:1.

For the etherification, the molar ratio of methanol and primary $C_3$- or $C_4$-alcohol to isobutene contained in the $C_4$-hydrocarbon mixture is in general from 100:1 to 0.7:1, preferably from 20:1 to 0.9:1, more especially from 4:1 to 1:1.

The etherification can be carried out in a single reaction stage or in several stages in series. In the latter case, in general 2 or 3 stages, preferably 2 stages, are employed.

The mixed $C_4$-hydrocarbon raffinate, consisting of the unconverted $C_4$-hydrocarbons, which is obtained by distillation may contain excess methanol added for carrying out the etherification, which, because of the formation of hydrocarbon/methanol azeotropes, also distils over during the distillative isolation of the mixed $C_4$-hydrocarbon raffinate. On the other hand, the raffinate is, surprisingly, virtually free from the primary $C_3$- or $C_4$-alcohol which may have been employed in excess for the etherification.

If the etherification is carried out in a single stage, the $C_4$-hydrocarbon mixture is advantageously reacted with a mixture of methanol and primary $C_3$- or $C_4$-alcohol. If, according to a preferred embodiment, the etherification is carried out in two successive stages, different alcohols may be employed in these, and in that case preferably methanol is employed in the first stage and the primary $C_3$- or $C_4$-alcohol in the second stage. However, it is also possible to employ mixtures of methanol and the tertiary $C_3$- or $C_4$-alcohol in both stages. Equally, it is possible to employ the mixture of the alcohols in the first stage and the primary $C_3$- or $C_4$-alcohol in the second stage, or the $C_3$- or $C_4$-alcohol or, preferably, methanol, in the first stage and the mixture of the alcohols in the second stage.

Preferably, if the process is carried out in two stages, a mixture of the alcohols, for example in a molar ratio of from 1:20 to 20:1, preferably from 1:10 to 10:1, especially from 1:5 to 5:1, is employed in the first etherification stage, whilst in the second etherification stage the proportion of $C_3$- or $C_4$-alcohol in the total amount of alcohol added to this stage is not less than 50 mole%, preferably not less than 80 mole%, especially not less than 90 mole%, and may even be 100 mole%.

The methanol contained in the top product (also containing the unconverted hydrocarbons) which is obtained, in two stage operation using methanol in the first stage, upon distillation of the reaction mixture from the first stage, can be removed, for example by a water wash, with or without subsequent drying, before the top product is transferred to the second etherification stage. Preferably, however, the top product is reacted further, in the second etherification stage, without having removed the methanol.

In two-stage operation, the isobutene-containing $C_4$-hydrocarbon starting mixture can be introduced, in its entirety, into the first stage, whilst the hydrocarbon mixture isolated from the reaction mixture of the first stage is fed to the second etherification stage. However, it can be advantageous only to feed a proportion, for example from 5 to 95%, of the $C_4$-hydrocarbon starting mixture to the first etherification stage and feed the remainder, advantageously after mixing it with unconverted $C_4$-hydrocarbons obtained from the first stage, to the second etherification stage. The reaction mixture from the second etherification stage is in general subjected to distillation, giving, as the top product, a $C_4$-hydrocarbon raffinate containing the unconverted hydrocarbons and having an isobutene content which is in general not more than 5% by weight, preferably not more than 3% by weight, in particular not more than 1% by weight. However, it is also possible to take off a $C_4$-hydrocarbon raffinate containing less than 0.5% by weight of isobutene.

Where the proportion of $C_3$- or $C_4$-alcohol in the total amount of alcohol added to the second stage is substantial, ie. not less than 50 mole%, preferably not less than 80 mole%, in particular not less than 90 mole%, or where exclusively $C_3$- or $C_4$-alcohol is added to the second etherification stage, for example when the reaction is carried out with the methanol-containing $C_4$-hydrocarbon raffinate obtained from the first etherification stage by distillation, the methanol concentration in the $C_4$-hydrocarbon raffinate obtained by distilling the reaction mixture of the second etherification stage can be lowered far below the concentration which corresponds to the azeotrope of methanol with the $C_4$-hydrocarbons, without it being necessary to interpolate a water wash. Preferably, a $C_4$-hydrocarbon raffinate containing less than 1% by weight, preferably less than 0.5% by weight, of methanol, and containing not more than 1,000 ppm by weight, preferably not more than 500 ppm by weight, in particular not more than 100 ppm by weight, of $C_3$- or $C_4$-alcohol, methyl tert.-butyl ether and $C_3$- or $C_4$-alkyl tert.-butyl ether is taken off. If the $C_4$-hydrocarbon raffinate is intended to be virtually methanol-free, it can be after-treated, for example by means of a water wash, or of a distillation under pressure, in general at not less than 10 bar, preferably at from 20 bar to the critical pressure of the $C_4$-hydrocarbons. As a rule, however, such an after-treatment is not necessary.

In a preferred embodiment of the process according to the invention, the etherification reaction is carried out as a one-stage or multi-stage, preferably 2-stage, operation, and in multi-stage operation the reaction with methanol is carried out in the very first stage; the reaction mixture from the etherification stage, or, in the case of multi-stage operation, the reaction mixture from the first etherification stage, is fed to a distillation zone with side take-off, from which take-off a methanol-rich fraction is obtained, which is advantageously recycled to the etherification stage or, in the case of multi-stage operation, to the first etherification stage. However, it is also possible to carry out the distillation without a side take-off.

In two-stage operation, the top product from the first distillation is advantageously a fraction which contains the unconverted hydrocarbons and, in general, from 1 to 5,000 ppm by weight, preferably from 10 to 2,000 ppm by weight, in particular from 50 to 1,000 ppm by weight, of methyl tert.-butyl ether; this fraction is fed to the second etherification stage. Furthermore, the top product as a rule contains more than 1.5% of methanol if the distillation is carried out in a conventional manner. The methanol can be removed by, for example, a water wash. However, in general the raffinate from the first stage is fed to the second stage direct, ie. without interpolating a water wash.

The bottom product which remains after distillative removal of the mixed $C_4$-hydrocarbon raffinate and which still contains methyl tert.-butyl ether, with or without methanol, primary $C_3$- or $C_4$-alcohol and the $C_3$- or $C_4$-alkyl tert.-butyl ether, is advantageously subjected to a further distillation, in which the methyl tert.-butyl ether and any methanol present are separated off, and, finally, a bottom product containing the $C_3$- or $C_4$-alkyl tert.-butyl ether, with or without $C_3$- or $C_4$-alcohol, is obtained. In general, the bottom product obtained contains less than 500 ppm by weight, preferably less than 100 ppm by weight, in particular less than 10 ppm by weight, of methanol and methyl tert.-butyl ether.

The resulting $C_3$- or $C_4$-alkyl tert.-butyl ether is subsequently decomposed into isobutene and primary $C_3$- or $C_4$-alcohol in the second stage of the process, at an elevated temperature and in the presence of an acid catalyst. The starting material used for the decomposition can be a tertiary ether which is virtually free from $C_3$- or $C_4$-alcohol, and which has been obtained, for example, by using, in the etherification, an amount of $C_3$- or $C_4$-alcohol which at most corresponds to the stoichiometrically required amount of alcohol, and removing, for example by distillation, any unconverted primary $C_3$- or $C_4$-alcohol from the bottom product ultimately obtained after distillation of the etherification reaction mixture. Preferably, the $C_3$- or $C_4$-alkyl tert.-butyl ether obtained as the bottom product after distillative removal of the mixed $C_4$-hydrocarbon raffinate and of the methyl tert.-butyl ether is employed for the decomposition without additionally removing any excess $C_3$- or $C_4$-alcohol which may be present. However, it is also possible to remove only a part of the excess $C_3$- or $C_4$-alcohol before carrying out the decomposition. Advantageously, the $C_3$- or $C_4$-alkyl tert.-butyl ether obtained as the bottom product contains less than 1,000 ppm by weight, preferably less than 100 ppm by weight, in particular less than 10 ppm by weight, of the unconverted $C_4$-hydrocarbons.

To carry out the decomposition, the tertiary ether is vaporized and brought into contact, as vapor, with the acid catalyst. Examples of suitable acid catalysts are ion exchangers in the hydrogen form, eg. sulfonated coal, sulfonated phenol-formaldehyde resins, sulfonated resins derived from coumarone-indene condensates, and, in particular, sulfonated polystyrene resins, eg. nuclear-sulfonated, crosslinked styrene-divinylbenzene copolymers.

Other advantageous catalysts include solid phosphoric acid catalysts, which contain monophosphoric acid or preferably polyphosphoric acid on a solid carrier. Examples of suitable carriers for the phosphoric acid catalysts are aluminum oxide, silica, active charcoal, kieselguhr or pumice. The preferred carrier is silica gel.

Further examples of suitable catalysts are acid metal sulfates, eg. sodium bisulfate, calcium bisulfate, aluminum sulfates, nickel sulfate, copper sulfate, cobalt sulfate, cadmium sulfate and strontium sulfate. These acid metal sulfates may be used unsupported but are preferably employed on a carrier. Examples of suitable carriers are silica gel, active charcoal, aluminum oxide and pumice.

Furthermore, silica gel or aluminum oxide by themselves may be used as catalysts for the decomposition.

In a further embodiment of the process according to the invention, a metal phosphate, in particular a metal hydrogen phosphate, is used as the acid catalyst for the decomposition. These phosphates may also contain an excess of phosphoric acid over what corresponds to the stoichiometric composition of the acid metal phosphate, for example an excess of up to 65%, preferably up to 20%, in particular up to 10%. Examples of suitable metal phosphates are magnesium phosphates, calcium phosphates, strontium phosphates, barium phosphates, manganese phosphates, nickel phosphates, copper phosphates, cobalt phosphates, cadmium phosphates, iron-(II) phosphates, chromium phosphates and, in particular, aluminum phosphates. The metal phosphate catalyst may be used as such or on a carrier. Examples of suitable carriers are aluminum oxide, silica, active charcoal and zinc oxide.

The amount of the acid catalyst is in general from about 0.01 to 1 kg, preferably from about 0.03 to 0.3 kg, per kg/h of tertiary ether put through the reactor. Preferably, a fixed bed reactor is used for the decomposition of the tertiary ether.

The temperature at which the tertiary ether is decomposed varies depending on the nature of the acid catalyst and on the contact time, but is in general from 50° to 350° C., preferably from 80° to 300° C., in particular from 100° to 250° C. If metal phosphates or phosphoric acid catalysts are used for the decomposition, the temperature employed is in general from 80° to 350° C., preferably from 90° to 260° C., especially from 100° to 250° C.

The time for which the vaporized tertiary ether is in contact with the catalyst is advantageously from 0.1 to 20 seconds, preferably from 1 to 10 seconds.

The decomposition of the tertiary ether can be carried out under atmospheric pressure. However, it is also feasible, and may be advantageous, to employ superatmospheric pressure, for example from 2 to 15 bar, preferably from 3 to 12 bar, especially from 4 to 12 bar. It is also possible to carry out the decomposition under reduced pressure. Whilst the decomposition of the tertiary ether can be carried out batchwise, it is preferably effected continuously.

The reaction mixture which is obtained from the decomposition and which contains isobutene and primary $C_3$- $C_4$-alcohol as the reaction products, is separated into the isobutene and the alcohol. Advantageously, this is done by distillation, whereby an isobutene which is more than 99.3% pure, preferably more than 99.8% pure, can be obtained in a simple manner, without interpolating a water wash. Advantageously, the very pure isobutene obtained without interpolating a water wash contains not more than 500 ppm by weight, preferably not more than 200 ppm by weight, in particular not more than 20 ppm by weight, of the $C_3$- or $C_4$-alcohol, and even contents of $C_3$- or $C_4$-alcohol of not more than 5 ppm by weight can be obtained by carrying out the distillative separation without any special measures.

The $C_3$- or $C_4$-alcohol obtained from the separation is in general recycled to the etherification. This recycled alcohol may, due to progressive accumulation, and without any particular disadvantage as far as the etherification is concerned, contain up to 30% by weight, preferably up to 15% by weight, in particular up to 10% by weight, of di-$C_3$- or $C_4$-alkyl ether, with or without up to 10% by weight, preferably up to 5% by weight, in particular up to 2% by weight, of $C_3$- or $C_4$-alkyl tert.-butyl ether or of isobutene or of each of these.

If the process is carried out continuously, and the primary $C_3$- or $C_4$-alcohol obtained after decomposition of the tertiary ether and subsequent working up of the reaction mixture is recycled to the etherification zone, it can be advantageous, in the novel process, if isobutanol is used as the $C_4$-alcohol, to take off an isobutanol part-stream from the recycled material in order to remove any accumulated impurities, such as diisobutyl ether. Advantageously, this part-stream is from 0.1 to 10% by weight, preferably from 0.5 to 5% by weight, of the total stream and in general contains from 3 to 40% by weight, preferably from 5 to 35% by weight, in particular from 10 to 30% by weight, of diisobutyl ether. In an advantageous embodiment of the process, the isobutanol part-stream is dehydrated to isobutene in a conventional manner in the presence of a dehydration catalyst, whereby the yield of isobutene can be additionally increased, in contrast to the conventional processes.

Advantageously, the dehydration is carried out in the gas phase over a catalyst. Examples of suitable catalysts are silica gel, thorium oxide, titanium(IV) oxide and especially aluminum oxide. In general, the dehydration temperature is from 250° to 450° C., preferably from 300° to 400° C.

The FIG. diagramatically illustrates an embodiment of the process according to the invention. The isobutene-containing $C_4$- hydrocarbon mixture (arriving through line 1) and the methanol, with or without primary $C_3$- or $C_4$-alcohol, eg. isobutanol (arriving through line 2), are mixed and the resulting mixture is fed through line 3 to the first etherification reactor 4, which contains the acid condensing agent, for example an ion exchanger. Advantageously, the reactor is a fixed bed reactor, for example a flow tube or a loop reactor or a combination of the two types. However, a different type of reactor, for example a stirred kettle or a stirred kettle cascade, may also be used. The reaction mixture obtained is taken from the reactor through line 5 and is fed to a first distillation column 6. At the top of the distillation column, a mixed $C_4$-hydrocarbon raffinate of low isobutene content is taken off through line 7. If appropriate, a methanol-containing fraction is taken off the side of column 6, and is recycled to the etherification reactor 4 through line 3. The raffinate from the first etherification stage, which has been taken off through line 7 and which contains unconverted $C_4$-hydrocarbons is mixed with isobutanol (from line 8) and the mixture is fed to a second etherification reactor 9, which can be of similar construction to the first etherification reactor. The product from the second etherification reactor 9 is fed through line 10 to a further distillation column 11. At the top of this column, a $C_4$-hydrocarbon raffinate which is substantially free from isobutene, alcohol and ether is taken off through line 12. The bottom products, containing the tertiary ethers formed, from distillation columns 6 and 11 are taken off through lines 13 and 14 and fed to the distillation column 15. It can be advantageous to introduce the two streams 13 and 14 at different points of the distillation column 15. At the top of this column, the methyl tert.-butyl ether is taken off through line 16, whilst the fraction containing the $C_3$- or $C_4$-alkyl tert.-butyl ether, and any excess $C_3$- or $C_4$-alcohol, is taken off at the bottom through line 17 and fed, as vapor, into the decomposition reactor 18. The products from the latter are fed through line 19 into the distillation column 20. At the top of this column, pure isobutene is taken off through line 21. At the bottom, the isobutanol obtained from the decomposition is taken off through line 22 and recycled, through lines 8 and 23, to the etherification.

EXAMPLE

The etherification was carried out using a $C_4$-hydrocarbon mixture consisting of the residue (raffinate) of a $C_4$-fraction which had been obtained from an ethylene plant and from which butadiene had been extracted. After the extraction of the butadiene, the composition of the $C_4$-hydrocarbon mixture was as follows:

| | |
|---|---|
| isobutane | 1.9% by volume |
| n-butane | 8.1% by volume |
| isobutene | 46.0% by volume |
| but-1-ene | 26.7% by volume |
| trans-but-2-ene | 10.1% by volume |
| cis-but-2-ene | 7.0% by volume |
| buta-1,3-diene | 0.2% by volume |

The $C_4$-hydrocarbon mixture, together with the stoichiometric amount (based on isobutene contained in the mixture) of a mixture of methanol and isobutanol in a molar ratio of 1:1, was fed to a first etherification reactor, which was in the form of a tubular reactor. The temperature profile in this reactor was such that the exit temperature of the reaction mixture from the reactor was 40° C, whilst the temperature in the reactor, in the vicinity of the feed point of the starting materials, was from 70° to 80° C. The pressure was 15 bar, so that the reaction took place in the liquid phase. The tubular reactor was completely packed with an ion exchanger in the hydrogen form (styrene-divinylbenzene copolymer resin, Lewatit S PC 118). The reaction mixture was separated in a distillation column with 15 trays (the mixture being fed onto the 10th tray). At the top of the column, a methanol-containing $C_4$-hydrocarbon mixture was taken off; this contained the unconverted hydrocarbons and less than 100 ppm by weight of each of the following: methyl tert.-butyl ether, isobutanol and isobutyl tert.-butyl ether. At the bottom, a mixture of the three last-mentioned compounds was taken off. A methanol-containing fraction was taken from the 5th tray and recycled to the first etherification stage.

The $C_4$-hydrocarbon mixture taken off at the top of the distillation column was mixed with a stoichiometric amount of isobutanol and the mixture was fed to a second etherification reactor. The temperature profile and pressure in this reactor were the same as in the first etherification reactor. The reaction product from the second etherification reactor was distilled in a second distillation column with 15 trays, the product being fed onto the 10th tray. At the top of the second distillation column, a $C_4$-hydrocarbon raffinate was taken off which contained less than 10 ppm of each of the following: isobutanol, isobutyl tert.-butyl ether and methyl tert.-butyl ether. The methanol content was about 0.5% by weight. The bottom product of the second distillation column was combined with the bottom product of the first distillation column. The combined bottom products contained less than 10 ppm of $C_4$-hydrocarbons and were separated, by distillation, into a methyl tert.-butyl ether fraction and a fraction containing isobutanol and isobutyl tert.-butyl ether. The latter fraction was then vaporized and fed into a tubular decomposition reactor. The decomposition temperature over the entire reactor was from 180° to 200° C., the exit temperature being about 200° C. The acid catalyst used was a silica gel which was impregnated with phosphoric acid and then heated. The residence time was about 3 seconds and the pressure was set to 5 bar.

The reaction product from the decomposition reactor was separated in a further distillation column with 15 trays, the product being fed onto the 10th tray. At the top of the column, isobutene which was more than 99.8% pure was taken off. The subsidiary components were n-butenes. The contents of isobutanol and isobutyl tert.-butyl ether in the top product were less than 10 ppm each. The methanol and methyl tert.-butyl ether had already been removed by distillation before the product was fed into the decomposition reactor, so that a water wash was unnecessary. The isobutene obtained was suitable for use in subsequent reactions, without additional purification. Isobutanol was recovered at the bottom of the distillation column and recycled to the etherification stages. The yield of isobutene and methyl tert.-butyl ether was more than 97.5%, based on the amount of isobutene in the $C_4$-hydrocarbon mixture employed.

We claim:

1. A process for conjointly preparing methyl tert.-butyl ether and obtaining isobutene from an isobutene-containing $C_4$-hydrocarbon mixture wherein
   (a) the $C_4$-hydrocarbon mixture is reacted, in one or more etherification stages, with methanol and a primary $C_3$- or $C_4$-alcohol in the presence of an acid condensing agent,
   (b) the resulting reaction mixture or the resulting reaction mixtures are then separated into
   a fraction containing the unconverted hydrocarbons,
   the methyl tert.-butyl ether and
   a fraction containing the $C_3$- or $C_4$-alkyl tert.-butyl ether and
   (c) thereafter the $C_3$- or $C_4$-alkyl tert.-butyl ether is decomposed at an elevated temperature, in the presence of an acid catalyst, into isobutene and primary $C_3$- or $C_4$-alcohol.

2. The process of claim 1, wherein an ion exchanger in the hydrogen form is used as the acid condensing agent for the formation of the ether.

3. The process of claim 1 or 2, wherein the $C_4$-hydrocarbon mixture is reacted in at least two successive etherification stages.

4. The process of claim 3, wherein methanol, or a mixture of methanol and the primary $C_3$- or $C_4$-alcohol, is employed in a first etherification stage, and the primary $C_3$- or $C_4$-alcohol is employed in a second etherification stage.

5. The process of claim 1 or 2, wherein the $C_4$-hydrocarbon mixture is reacted with a mixture of methanol and primary $C_3$- or $C_4$-alcohol in the first stage.

6. The process of claim 3, wherein the $C_4$-hydrocarbon mixture is reacted with a mixture of methanol and the primary $C_3$- or $C_4$-alcohol in each of two successive etherification stages, the ratio of the amount of methanol fed to the first etherification stage to the amount of primary $C_3$- or $C_4$-alcohol fed to the first etherification stage being greater than the corresponding ratio of materials fed to the second etherification stage.

7. The process of claim 1 or 2 or wherein the etherification reaction is carried out in one stage, and the reaction mixture from the etherification stage is fed to a distillation zone with side take-off, in which zone a fraction containing the unconverted $C_4$-hydrocarbons is taken off at the top, a fraction containing the tertiary ether formed is taken off at the bottom and a fraction containing the unconverted methanol is taken off at the side, the last-mentioned fraction being recycled to the etherification stage.

8. The process of claim 1 or 2, wherein the $C_4$-hydrocarbon mixture is reacted in two successive etherification stages and wherein the reaction mixture from the second etherification stage is subjected to a distillation, in which the top product taken off is a fraction which contains the unconverted $C_4$-hydrocarbons, together with not more than 1% by weight of methanol and not more than 1,000 ppm by weight of each of the following: $C_3$- or $C_4$-alcohol, methyl tert.-butyl ether and $C_3$- or $C_4$-alkyl tert.-butyl ether.

9. The process of claim 1 or 2, wherein the reaction mixture which is obtained on decomposition of the $C_3$- or $C_4$-alkyl tert.-butyl ether (containing any excess added primary $C_3$- or $C_4$-alcohol), and which contains isobutene and the primary $C_3$- or $C_4$-alcohol, is fed to a distillation zone in which-without interpolating a water wash-isobutene containing not more than 500 ppm by weight of primary $C_3$- or $C_4$-alcohol is taken off at the top, while the bottom product obtained, which contains the primary $C_3$- or $C_4$-alcohol, is recycled to the etherification.

10. The process of claim 1 or 2 wherein the etherification reaction is carried out in two stages, and the reaction with methanol is carried out in the first stage, and the reaction mixture from the first etherification stage is fed to a distillation zone with side take-off, in which zone a fraction containing the unconverted $C_4$-hydrocarbons is taken off at the top, a fraction containing the tertiary ether formed is taken off at the bottom and a fraction containing the unconverted methanol is taken off at the side, the last-mentioned fraction being recycled to the first etherification stage.

11. The process of claim 1 or 2, wherein the weight ratio of methanol to $C_3$- or $C_4$-alcohol employed in the process is from 1:2 to 20:1.

12. The process of claim 11 wherein the molar ratio of methanol and $C_3$- or $C_4$-alcohol to isobutene contained in the $C_4$-hydrocarbon mixture is from 20:1 to 0.9:1.

* * * * *